United States Patent
Ajima

(10) Patent No.: US 10,390,761 B2
(45) Date of Patent: Aug. 27, 2019

(54) DEVICE, DEVICE CONTROL METHOD AND CONTROL PROGRAM, AND SYSTEM

(71) Applicant: KYOCERA CORPORATION, Kyoto (JP)

(72) Inventor: Hiromi Ajima, Kanagawa (JP)

(73) Assignee: KYOCERA Corporation, Kyoto (JP)

( * ) Notice: Subject to any disclaimer, the term of this patent is extended or adjusted under 35 U.S.C. 154(b) by 223 days.

(21) Appl. No.: 14/784,741

(22) PCT Filed: Apr. 15, 2014

(86) PCT No.: PCT/JP2014/060761
§ 371 (c)(1),
(2) Date: Oct. 15, 2015

(87) PCT Pub. No.: WO2014/171465
PCT Pub. Date: Oct. 23, 2014

(65) Prior Publication Data
US 2016/0058385 A1    Mar. 3, 2016

(30) Foreign Application Priority Data

Apr. 16, 2013   (JP) .................................. 2013-085964
Aug. 28, 2013   (JP) .................................. 2013-177107
(Continued)

(51) Int. Cl.
*A61B 5/00*   (2006.01)
*A61B 5/022*  (2006.01)
(Continued)

(52) U.S. Cl.
CPC ............ *A61B 5/6898* (2013.01); *A61B 5/022* (2013.01); *A61B 5/02007* (2013.01);
(Continued)

(58) Field of Classification Search
None
See application file for complete search history.

(56) References Cited

U.S. PATENT DOCUMENTS

2003/0167014 A1    9/2003   Ogura
2004/0044288 A1*   3/2004   Gorenberg ......... A61B 5/02141
                                                                600/481
(Continued)

FOREIGN PATENT DOCUMENTS

JP    H07-37104 U     7/1995
JP    H10-211172 A    8/1998
(Continued)

OTHER PUBLICATIONS

An Office Action; "Notice of Reasons for Rejection," issued by the Japanese Patent Office dated Feb. 28, 2017, which corresponds to Japanese Patent Application No. 2016-195664 and is related to U.S. Appl. No. 14/784,741; with English language Concise Explanation.
(Continued)

*Primary Examiner* — Jacqueline Cheng
*Assistant Examiner* — Jay B Shah
(74) *Attorney, Agent, or Firm* — Studebaker & Brackett PC

(57) ABSTRACT

Provided is a device which can utilize a motion sensor installed in a mobile device. A smartphone includes a motion sensor and a controller. The motion sensor detects a motion factor. The controller processes the motion factor detected by the motion sensor as a self-control factor. The controller can process the motion factor detected by the motion sensor as a vital-sign factor of a user.

2 Claims, 10 Drawing Sheets

(30) Foreign Application Priority Data

Jan. 30, 2014 (JP) .................................. 2014-016044
Feb. 27, 2014 (JP) .................................. 2014-036931

(51) Int. Cl.
*A61B 5/0245* (2006.01)
*A61B 5/11* (2006.01)
*A61B 5/02* (2006.01)
*A61B 5/021* (2006.01)

(52) U.S. Cl.
CPC ........ *A61B 5/0245* (2013.01); *A61B 5/02108* (2013.01); *A61B 5/1118* (2013.01); *A61B 5/7278* (2013.01); *A61B 2562/0219* (2013.01)

(56) References Cited

U.S. PATENT DOCUMENTS

| | | | |
|---|---|---|---|
| 2006/0139930 A1* | 6/2006 | Feinsod | G02B 27/20 362/276 |
| 2008/0190202 A1* | 8/2008 | Kulach | A63B 24/0062 73/514.01 |
| 2009/0306523 A1 | 12/2009 | Saito et al. | |
| 2011/0054329 A1* | 3/2011 | Katsumoto | A61B 5/021 600/490 |
| 2011/0065482 A1 | 3/2011 | Koide et al. | |
| 2011/0077865 A1* | 3/2011 | Chen | A61B 5/1117 702/3 |
| 2014/0194756 A1 | 7/2014 | Sazuka | |

FOREIGN PATENT DOCUMENTS

| | | |
|---|---|---|
| JP | 2001-272413 A | 10/2001 |
| JP | 2002-017693 A | 1/2002 |
| JP | 2003-070752 A | 3/2003 |
| JP | 2003-250769 A | 9/2003 |
| JP | 2004-321252 A | 11/2004 |
| JP | 2006-107657 A | 4/2006 |
| JP | 2006-255374 A | 9/2006 |
| JP | 2008-29690 A | 2/2008 |
| JP | 2008-086568 A | 4/2008 |
| JP | 2012-105762 A | 6/2012 |
| JP | 2012-239799 A | 12/2012 |
| WO | 2009/139244 A1 | 11/2009 |

OTHER PUBLICATIONS

An Office Action; "Notice of Reasons for Rejection," issued by the Japanese Patent Office dated Mar. 7, 2017, which corresponds to Japanese Patent Application No. 2015-512493 and is related to U.S. Appl. No. 14/784,741; with English language Concise Explanation.
JP Office Action dated Nov. 15, 2016 from corresponding JP Appl No. 2016-195663, with concise statement of relevance, 3 pp.
JP Office Action dated Nov. 22, 2016 from corresponding JP Appl No. 2015-512493, with concise statement of relevance, 4 pp.
International Search Report issued in PCT/JP2014/060761; dated Jun. 24, 2014.

* cited by examiner

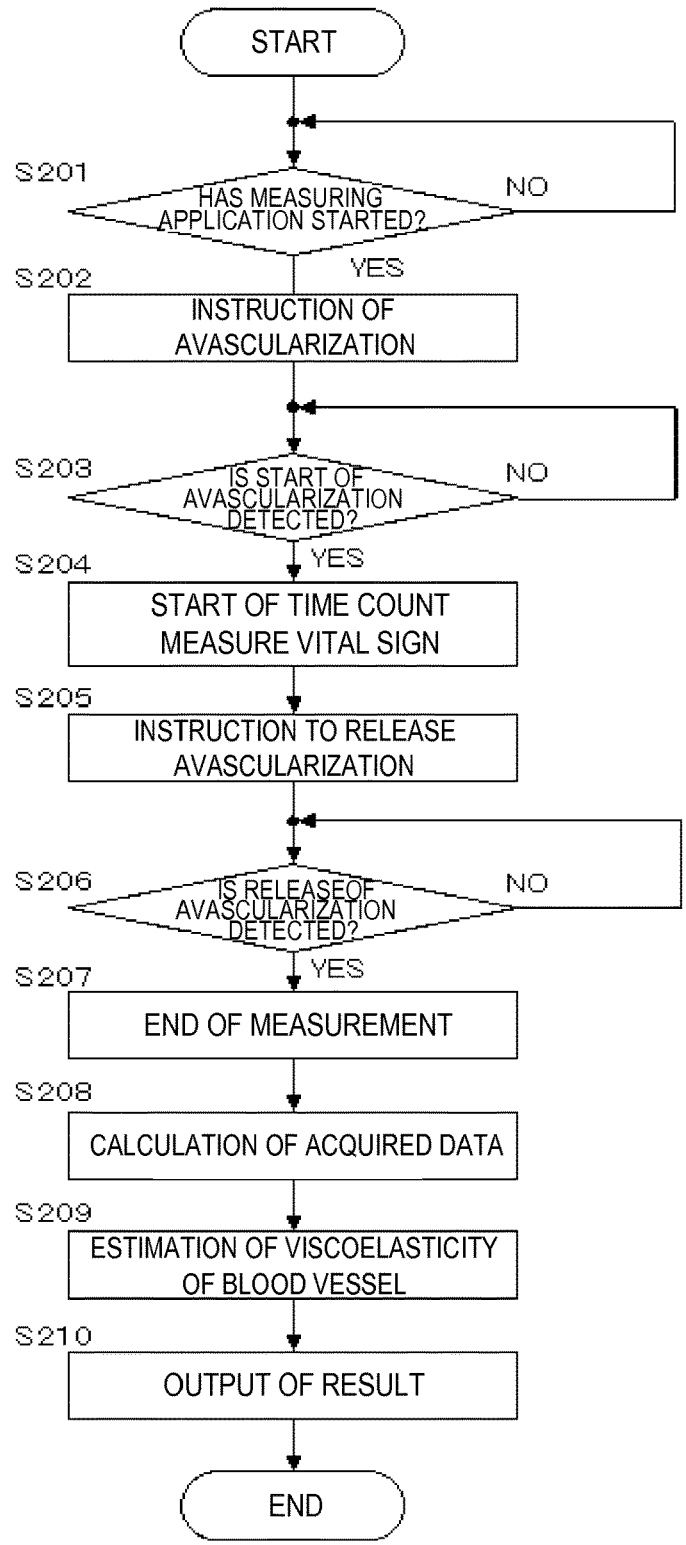

DEVICE, DEVICE CONTROL METHOD AND CONTROL PROGRAM, AND SYSTEM

CROSS-REFERENCE TO RELATED APPLICATION

This application claims priority from PCT Application No. PCT/JP14/060761 filed on Apr. 15, 2014, the entire subject matter of which is incorporated herein by reference.

TECHNICAL FIELD

This disclosure relates to a device, a control method and a control program of a device, and a system.

BACKGROUND ART

A device having an acceleration sensor is known. The device having an acceleration sensor includes a smartphone and a mobile phone, for example. In the device having an acceleration sensor, detected acceleration is used for a variety of control. An example in which detected acceleration is used for state control in dropping is described in Patent Literature 1. In mobile phones according to the background art including the mobile phone described in Patent Literature 1, an acceleration sensor is used to detect a state of a mobile phone itself.

CITATION LIST

Patent Literature

Patent Literature 1: Japanese Unexamined Patent Application Publication No. 2006-107657

SUMMARY

An object of this disclosure is to provide a device, a control method, and a control program which can utilize a motion sensor installed therein.

A device according to an embodiment of this disclosure includes: a motion sensor, which detects a motion factor; and a controller, which processes the motion factor detected by the motion sensor as a self-control factor, wherein the controller processes the motion factor detected by the motion sensor as a vital-sign factor of a user.

A control method of a device according to an embodiment of the present invention, the device including a motion sensor, which detects a motion factor and a controller, which processes the motion factor detected by the motion sensor as a self-control factor, the control method includes: causing the controller to process the motion factor detected by the motion sensor as a vital-sign factor of a user.

A control method of a device according to an embodiment of this disclosure, the device including a motion sensor, which detects at least one of acceleration and angular velocity and a controller, which processes a motion factor detected by the motion sensor as a self-control factor, the control method includes: causing the controller to process the motion factor detected by the motion sensor as a vital-sign factor of a user.

A non-transitory computer-readable medium having instructions to control a device according to an embodiment of this disclosure, the device including a motion sensor, which detects a motion factor and a controller, which processes the motion factor detected by the motion sensor as a self-control factor, the instructions controls the controller to process the motion factor detected by the motion sensor as a vital-sign factor of a user.

According to this disclosure, it is possible to utilize a motion sensor installed in a device.

BRIEF DESCRIPTION OF THE DRAWINGS

FIG. 15 is a view illustrating an example of a control flow which is performed by a smartphone according to a second embodiment.

DETAILED DESCRIPTION

Embodiments of will be described in detail below with reference to the accompanying drawings. In the following description, a smartphone will be described as an example of a device.

Figure 1:
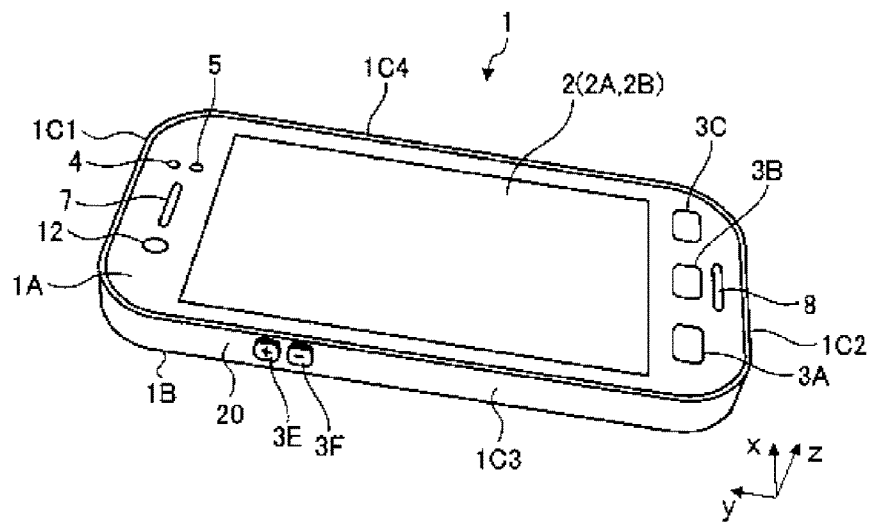
FIG. 1 is a perspective schematic view illustrating an appearance of a smartphone according to an embodiment.
Figure 2:
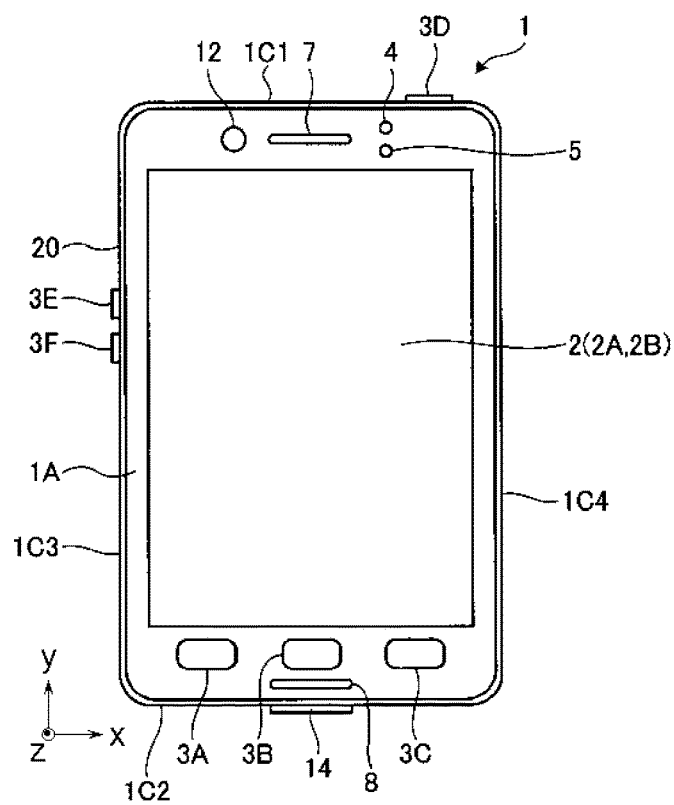
FIG. 2 is a front schematic view illustrating the appearance of the smartphone according to the embodiment.
Figure 3:
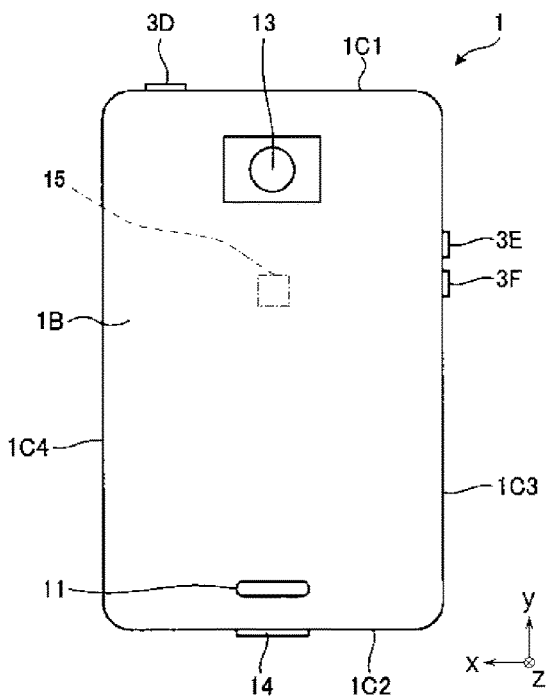
FIG. 3 is a rear schematic view illustrating the appearance of the smartphone according to the embodiment.

The appearance of a smartphone 1 according to an embodiment will be described with reference to FIGS. 1 to 3. As illustrated in FIGS. 1 to 3, the smartphone 1 includes a housing 20. The housing 20 includes a front face 1A, a back face 1B, and side faces 1C1 to 1C4. The front face 1A is a front surface of the housing 20. The back face 1B is a back surface of the housing 20. The side faces 1C1 to 1C4 are side surfaces connecting the front face 1A and the back face 1B. In the following description, the side faces 1C1 to 1C4 may be collectively referred to as a side face 1C without being specified.

The smartphone 1 includes a touch screen display 2, buttons 3A to 3C, an illuminance sensor 4, a proximity sensor 5, a receiver 7, a microphone 8, and a camera 12 on the front face 1A. The smartphone 1 includes a camera 13 on the back face 1B. The smartphone 1 includes buttons 3D to 3F and a connector 14 on the side face 1C. In the following description, the buttons 3A to 3F may be collectively referred to as a button 3 without being specified.

The touch screen display 2 includes a display 2A and a touch screen 2B. The display 2A includes a display device such as a liquid crystal display, an organic electro-luminescence (EL) panel, or an inorganic EL panel. The display 2A displays characters, images, symbols, figures, or the like.

The touch screen 2B detects a touch of a finger, a stylus pen, or the like with the touch screen 2B. The touch screen 2B can detect a position at which plural fingers, stylus pens, or the like touch the touch screen 2B.

The sensing system of the touch screen 2B may be any sensing system such as a capacitive system, a resistive membrane system, a surface acoustic wave system (or an ultrasonic system), an infrared system, an electromagnetic induction system, and a load detection system. In the capacitive system, a touch and an approach of a finger, a stylus pen, or the like can be detected. In the following description, for the purpose of simplification of explanation, the finger, the stylus pen, or the like of which the touch is sensed by the touch screen 2B may be simply referred to as a "finger."

The smartphone 1 determines a type of a gesture based on a touch sensed by the touch screen 2B, a position at which the touch is performed, a time in which the touch is performed, and a time-dependent variation of the touched position. A gesture is an operation which is performed on the touch screen display 2. Examples of the gesture determined by the smartphone 1 include a touch, a long touch, a release, a swipe, a tap, a double tap, a long tap, a drag, a flick, a pinch-in, and a pinch-out.

The touch is a gesture where a finger touch the touch screen 2B. The smartphone 1 determines the gesture where the finger touches the touch screen 2B as a touch. The long touch is a gesture where a finger touches the touch screen 2B for a predetermined time or more. The smartphone 1 determines the gesture where a finger touches the touch screen 2B for a predetermined time or more, as a long touch. The release is a gesture where a finger is detached from the touch screen 2B. The smartphone 1 determines the gesture where a finger is detached from the touch screen 2B, as a release.

The tap is a gesture where the release is performed subsequent to the touch. The smartphone 1 determines the gesture where the release is performed subsequent to the touch as a tap. The double tap is a gesture where the gesture where the release is performed subsequent to the touch is continuously performed two times. The smartphone 1 determines the gesture where the gesture where the release is performed subsequent to the touch is continuously performed two times, as a double tap. The long tap is a gesture where the release is performed subsequent to the long touch. The smartphone 1 determines the gesture where the release is performed subsequent to the long touch, as a long tap.

The swipe is a gesture where a finger moves while the finger is touching the touch screen display 2. The smartphone 1 determines the gesture where a finger moves while the finger is touching the touch screen display 2, as a swipe. The drag is a gesture where the swipe is performed with an area in which a movable object is displayed as a start point.

The smartphone 1 determines the gesture where the swipe is performed with an area in which a movable object is displayed as a start point, as a drag.

The flic is a gesture where a finger moves fast in one direction subsequently to a touch and the release is performed. The smartphone 1 determines the gesture where a finger moves fast in one direction subsequently to a touch and the release is performed, as a flick. The flick includes an upward flick in which a finger moves upward on the screen, a downward flick in which a finger moves downward on the screen, a right flick in which a finger moves rightward on the screen, and a left flick in which a finger moves leftward on the screen.

The pinch-in is a gesture where plural fingers swipe in a direction in which the fingers approach each other. The smartphone 1 determines the gesture where plural fingers swipe in a direction in which the fingers approach each other, as a pinch-in. The pinch-out is a gesture where plural fingers swipe in a direction in which the fingers get apart from each other. The smartphone 1 determines the gesture where plural fingers swipe in a direction in which the fingers get apart from each other, as a pinch-out.

The smartphone 1 performs an operation depending on the gestures which are determined by the touch screen 2B. In the smartphone 1, since an operation based on a gesture is performed, operability with which the smartphone can be easily intuitively used by a user is realized. The operation which is performed by the smartphone 1 based on the determined gesture differs depending on a screen displayed on the touch screen display 2.

Figure 4:
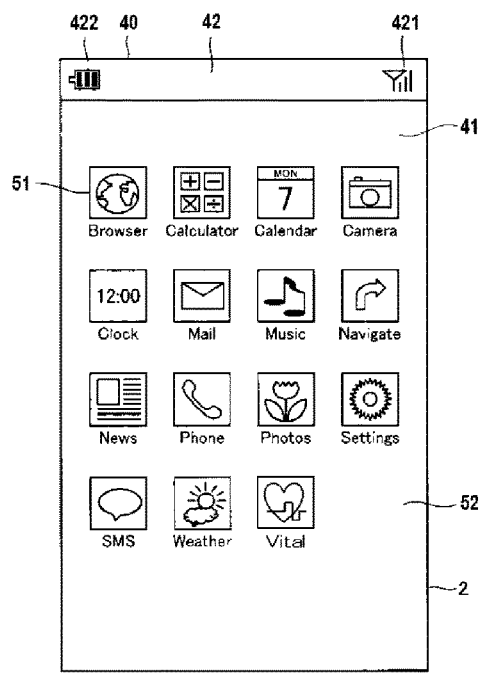
FIG. 4 is a view illustrating an example of a home screen.

An example of the screen displayed on the display 2A will be described below with reference to FIG. 4. FIG. 4 illustrates an example of a home screen. The home screen may be referred to as a desktop, a launcher, or an idle screen. The home screen is displayed on the display 2A. The home screen is a screen allowing a user to select an application to be executed among applications installed in the smartphone 1. The smartphone 1 executes the application selected from the home screen in the foreground. The screen of the application executed in the foreground is displayed on a display area 40 of the display 2A.

The smartphone 1 can arrange icons on the home screen. The home screen 50 illustrated in FIG. 4 is displayed in a first area 41 of the display area of the display 2A. Plural icons 51 are arranged on the home screen 50. The respective icons 51 are associated with the applications installed in the smartphone 1 in advance. When a gesture on an icon 51 is detected, the smartphone 1 executes the application associated with the icon 51. For example, when a tap on the icon 51 associated with a mail application is detected, the smartphone 1 executes the mail application.

For example, when a click on the button 3B is detected in a state where the mail application is executed in the foreground, the smartphone 1 displays the home screen 50 in the first area 41 of the display 2A and executes the mail application in the background. When a tap on an icon 51 associated with a browser application is detected, the smartphone 1 executes the browser application in the foreground. The application which is executed in the background can be stopped or ended depending on the execution state of the application or another application.

An icon 51 includes an image and a character string. The icon 51 may include a symbol or a figure instead of the image. The icon 51 may not include any one of an image and a character string. The icons 51 are arranged in accordance with a predetermined rule. A wallpaper 52 is displayed in the back of the icons 51. The wallpaper may be referred to as a photo screen or a back screen. The smartphone 1 can use any image as the wallpaper 52. Regarding the image, any image is determined as the wallpaper 52, for example, depending on a user's setting.

The smartphone 1 can increase or decrease the number of home screens. The smartphone 1 determines the number of home screens, for example, depending on the user's setting. The smartphone 1 displays one selected home screen on the display 2A even when the number of home screens is plural. Alternatively, when a gesture is detected in displaying a home screen, the smartphone 1 switches the home screen displayed on the display 2A. For example, when a right flick is detected, the smartphone 1 switches the home screen displayed on the display 2A to an immediately-left home screen. When a left flick is detected, the smartphone 1 switches the home screen displayed on the display 2A to an immediately-right home screen.

A second area 42 is disposed on the upper end of the display area 40 of the display 2A. In the second area 42, a residual capacity mark 421 indicating residual capacity of a storage battery and a radio wave level mark 422 indicating electric field intensity of communication a radio wave are displayed. The smartphone 1 may display a current time, weather information, an application under execution, a type of a communication system, a call status, a mode of a device, an event occurring in the device, and the like in the second area 42. The second area 42 is used to notify a user of various notices. The second area 42 may be installed on a screen other than the home screen 50. The position at which the second area 42 is installed is not limited to the upper end of the display 2A.

Now, the vertical direction of the home screen 50 will be described. The vertical direction of the home screen 50 is a direction based on the vertical direction of characters or images which are displayed on the display 2A. Accordingly, in the home screen 50, the side which is closer to the second area 42 in the longitudinal direction of the touch screen display 2 is set as an upper side of the home screen 50 and the side which is farther from the second area 42 is set as a lower side of the home screen 50. The side on which the radio wave level mark 422 is displayed in the second area 42 is a right side of the home screen 50, and the side on which the residual capacity mark 421 is displayed in the second area 42 is a left side of the home screen 50.

The home screen 50 illustrated in FIG. 4 is an example, and the shapes of various elements, the arrangements of various elements, the number of home screens 50, and various operation methods on the home screen 50 may not be limited to the above description.

Figure 5:
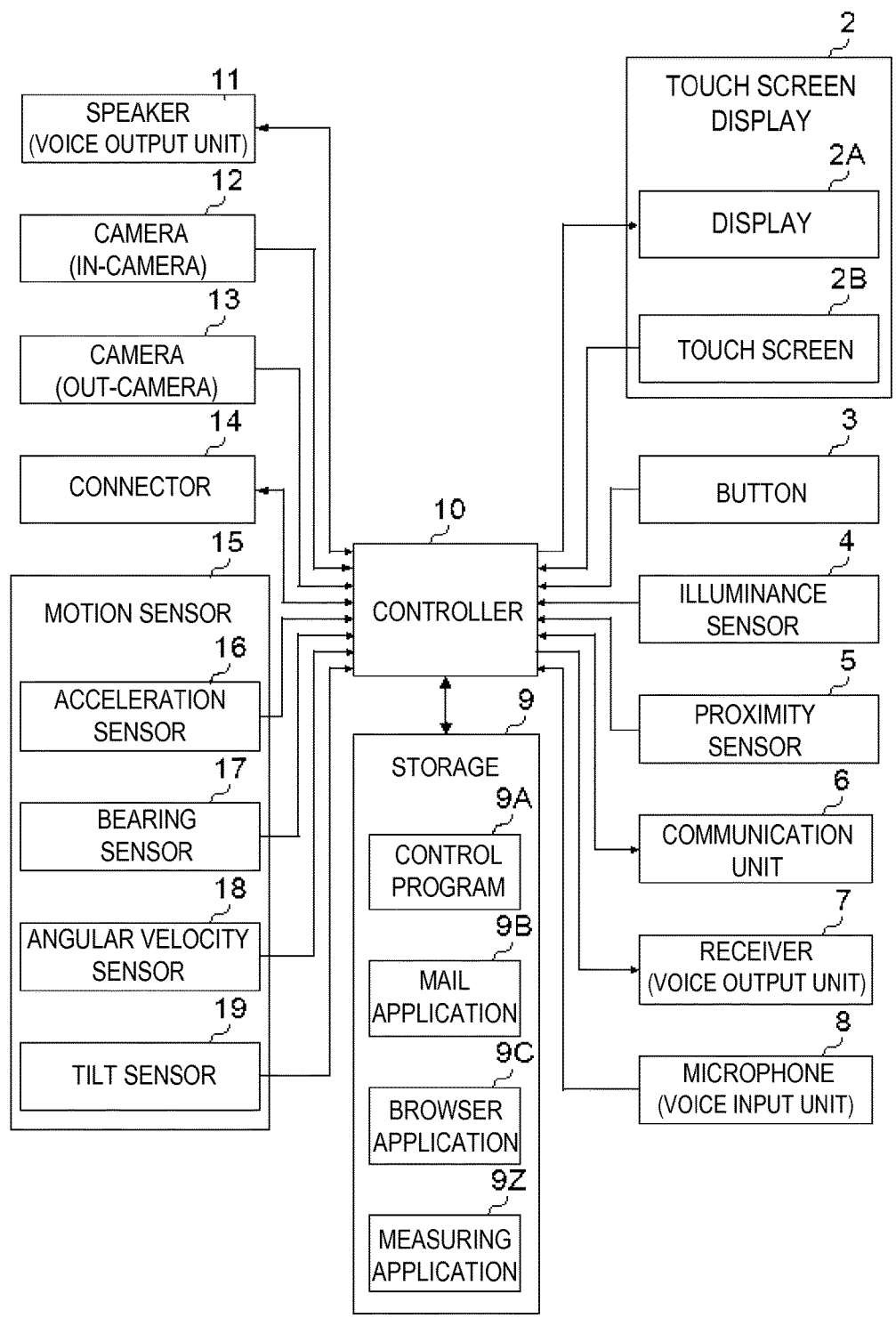
FIG. 5 is a schematic block diagram illustrating functions of the smartphone according to the embodiment.

FIG. 5 is a block diagram illustrating the configuration of the smartphone 1. The smartphone 1 includes the touch screen display 2, the buttons 3, the illuminance sensor 4, the proximity sensor 5, a communication unit 6, the receiver 7, the microphone 8, a storage 9, a controller 10, the cameras 12 and 13, the connector 14, and a motion sensor 15.

As described above, the touch screen display 2 includes the display 2A and the touch screen 2B. The display 2A displays characters, images, symbols, figures, and the like. The touch screen 2B receives a touch with a reception area as an input. That is, the touch screen 2B detects a touch. The controller 10 detects a gesture on the smartphone 1. The controller 10 detects an operation (gesture) on the touch screen 2B (the touch screen display 2) in cooperation with the touch screen 2B. The controller 10 detects an operation (gesture) on the display 2A (the touch screen display 2) in cooperation with the touch screen 2B.

The buttons 3 are operated by a user. The buttons 3 include buttons 3A to 3F. The controller 10 detects an operation on a button in cooperation with the buttons 3. Examples of the operation on a button include a click, a double click, a push, a long push, and a multi-plush.

For example, the buttons 3A to 3C are a home button, a back button, and a menu button. In this embodiment, touch sensor type buttons are employed as the buttons 3A to 3C. For example, the button 3D is a power-on/off button of the smartphone 1. The button 3D may also serve as a sleeve/sleeve-release button. For example, the buttons 3E and 3F are sound volume buttons.

The illuminance sensor 4 detects illuminance. For example, illuminance is intensity of light, brightness, luminance, or the like. For example, the illuminance sensor 4 is used to adjust luminance of the display 2A. The proximity sensor 5 detects presence of an object in the proximity in a noncontact manner. For example, the proximity sensor 5 detects that the touch screen display 2 gets close to a face.

The communication unit 6 communicates in a wireless manner. The communication system which is performed by the communication unit 6 is a wireless communication standard. Examples of the wireless communication standard include communication standards of a cellular phone such as 2G, 3G, and 4G. Examples of the communication standard of a cellular phone include LTE (Long Term Evolution), W-CDMA, CDMA2000, PDC, GSM (registered trademark), and PHS (Personal Handy-phone System). Examples of the wireless communication standard include WiMAX (Worldwide Interoperability for Microwave Access), IEEE802.11, Bluetooth (registered trademark), IrDA, and NFC. The communication unit 6 may support one or more of the above-mentioned communication standards.

The receiver 7 outputs a voice signal transmitted from the controller 10 as voice. The microphone 8 converts voice of users into voice signals and transmits the voice signals to the controller 10. The smartphone 1 may further include a speaker in addition to the receiver 7. The smartphone 1 may additionally include a speaker instead of the receiver 7.

The storage 9 stores programs and data. The storage 9 is also used as a work area that temporarily stores process results of the controller 10. The storage 9 may include any memory device such as a semiconductor memory device and a magnetic memory device. The storage 9 may include plural types of memory devices. The storage 9 may include a combination of a portable storage medium such as a memory card and a reader of a storage medium.

The programs stored in the storage 9 include applications which are executed in the foreground or in the background and a basic program supporting operations of the applications. For example, an application displays a predetermined screen on the display 2A and causes the controller 10 to perform a process based on a gesture detected using the touch screen 2B. An example of a basic program is an OS. The applications and the basic programs may be installed in the storage 9 by wireless communication of the communication 6 or via a storage medium.

The storage 9 stores, for example, a basic program 9A, a mail application 9B, a browser application 9C, and a vital-sign measuring application 9Z. The mail application 9B provides electronic mail functions for preparing, transmitting, receiving, and displaying, etc., an electronic mail. The browser application 9C provides a WEB browsing function for displaying a WEB page. The measuring application 9Z provides a function of measuring a vital sign as numerical information indicating a current state of a human body of a user using the smartphone 1. Here, the vital sign is an index indicating a living state. In this embodiment, the vital sign is a biological sign of a user such as a pulsating force, a pulse, a heartbeat, a motion accompanied with respiration, a blood pressure, a pulse pressure, and a variation accompanied with pulsation. In this embodiment, the vital sign is calculated from a vital-sign factor detected by the motion sensor. The vital sign is measured and calculated under the control of the controller 10.

The basic program 9A provides functions associated with a variety of control for activating the smartphone 1. The basic program 9A realizes a call, for example, by controlling the communication unit 6, the receiver 7, and the microphone 8. The functions provided by the basic program 9A may be used in combination with functions provided by other programs such as the mail application 9B.

The controller 10 is, for example, a central processing unit (CPU). The controller 10 may be an integrated circuit such as a system-on-a-chip (SoC) in which other elements such as the communication unit 6 are combined. The controller 10 collectively controls the operations of the smartphone 1 and realizes various functions.

Specifically, the controller 10 realizes various functions by executing commands included in the programs stored in the storage 9 with reference to data stored in the storage 9 as necessary and controlling the display 2A, the communication unit 6, and the like. The controller 10 can change the control depending on the detection results of various detection units such as the touch screen 2B, the buttons 3, and the motion sensor 15. The controller 10 according to this embodiment can change the control mode, in which the control is performed, to a first mode and a second mode depending on the detection results of various detection units. The control mode can be changed when the detection target of the detection results of various detection units is changed.

The camera 12 is an in-camera that captures an image of an object facing the front face 1A. The camera 13 is an out-camera that captures an image of an object facing the back face 1B.

The connector 14 is a terminal to which another device is connected. The connector 14 may be a universal terminal such as universal serial bus (USB), HDMI (registered trademark), mobile high-definition link (MHL), light peak, Thunderbolt (registered trademark), and earphone-microphone connector. The connector 14 may be a terminal which is designed dedicated purpose such as a Dock connector. Examples of the device connected to the connector 14 include a charger, an external storage, a speaker, a communication device, and an information processing device.

The motion sensor 15 detects a motion factor. The motion factor is processed as a control factor of the smartphone 1 which is a self-device by the controller 10. The controller 10 processes the motion factor detected by the motion sensor 15 as a control factor indicating a situation of the self-device. The motion sensor 15 in this embodiment includes an acceleration sensor 16, a bearing sensor 17, an angular velocity sensor 18, and a tilt sensor 19.

The acceleration sensor 16 detects acceleration acting on the smartphone 1. The acceleration sensor 16 outputs the detected acceleration. For example, when the direction of acceleration is output as the motion factor, the controller 10 can use the direction of acceleration to process a control factor reflecting the direction in which the smartphone 1 moves. For example, when the magnitude of acceleration is output, the controller 10 can use the magnitude of acceleration for process a control factor reflecting the direction in which the smartphone 1 moves. In this embodiment, a sensor capable of detecting acceleration in three axis directions is employed as the acceleration sensor 16. Three axis directions which are detected by the acceleration sensor 16 in this embodiment are substantially orthogonal to each other. The x direction, the y direction, and the z direction illustrated in FIGS. 1 to 3 correspond to the three axis directions of the acceleration sensor 16.

The bearing sensor 17 detects the direction of geomagnetism. The bearing sensor 17 outputs the detected direction of geomagnetism. For example, when the direction of geomagnetism is output as a motion factor, the controller 10 can use the direction of geomagnetism for processing a control factor reflecting the direction which the smartphone 1 faces. For example, when a variation in the direction of geomagnetism is output as a motion factor, the controller 10 can use the variation in the direction of geomagnetism for processing a control factor reflecting the variation in the direction which the smartphone 1 faces.

The angular velocity sensor 18 detects the angular velocity of the smartphone 1. The angular velocity sensor 18 outputs the detected angular velocity. For example, when presence of the angular velocity is output as a motion factor, the controller 10 can use the angular velocity for processing a control factor reflecting the rotation of the smartphone 1. For example, when the direction of the angular velocity is output as a motion factor, the controller 10 can use the direction of the angular velocity to process a control factor reflecting the rotation direction of the smartphone 1. In this embodiment, a sensor capable of detecting the angular velocity in three axis directions is employed as the angular velocity sensor 18. The x direction, the y direction, and the z direction illustrated in FIGS. 1 to 3 correspond to the three axis directions of the angular velocity sensor 18.

The tilt sensor 19 detects a tilt of the smartphone 1 with respect to the gravitational direction. The tilt sensor 19 outputs the detected tilt. For example, when the tilt with respect to the gravitational direction is output as a motion factor, the controller 10 can use the tilt to process a control factor reflecting the tilt of the smartphone 1.

The outputs of the acceleration sensor 16, the bearing sensor 17, the angular velocity sensor 18, and the tilt sensor 19 of the motion sensor 15 can be used in combination with each other. By combining and processing the outputs of the motion sensor 15, the controller 10 can perform processes reflecting the motion of the smartphone 1 as a self-device with a high degree.

In this embodiment, at least one of the acceleration sensor 16 and the angular velocity sensor 18 which are included in the motion sensor 15 is used to detect the motion factor of the smartphone 1. In other words, the motion factor in this embodiment includes at least one of the acceleration and the angular velocity. The smartphone 1 processes the motion factor as a control factor reflecting at least one of a posture variation, a position variation, and a direction variation. The control factor is processed by the controller 10. In this embodiment, the variation in the tilt in three axis directions of the smartphone 1 with respect to the gravitational direction is used as the posture variation.

An example in which the motion factor is used as a control factor of the posture variation is a process of changing a display direction of a screen. In the smartphone 1, the x axis direction and the y axis direction are compared, and the display direction of the screen is changed so as to display the screen along the axis direction closer to the gravitational direction. In changing the display direction of the screen, the motion factor is processed as a control factor to determine the physical direction of the screen in the smartphone 1.

An example in which the motion factor is used as a control factor of the position variation is a process of updating the position of the smartphone 1 in a place where GPS signals are not received. In updating the position, the motion factor is processed as a control factor to calculate a moving distance in the smartphone 1. This process is not limited to a place where GPS signals are not received and can be performed along with the GPS signals so as to enhance positional accuracy.

An example in which the motion factor is used as a control factor of the direction variation is a process of updating the direction of the smartphone 1 in a place where geomagnetism is not detected. In updating the direction variation, the motion factor is processed as a control factor to calculate a degree of axial rotation in the smartphone 1. This process is not limited to a place where geomagnetism is not detected and can be performed along with the detection signal of geomagnetism so as to enhance directional accuracy.

In this embodiment, the process based on the motion factor differs depending on a case when the control mode of the controller 10 is a first mode or a case when the control mode is a second mode. In the first mode, the detected motion factor is a state variation including at least one of the position variation, the direction variation, and the posture variation of the smartphone 1 and is processed as a control factor (self-control factor) of the self-device. In the second mode, the detected motion factor is processed as a vital-sign factor of a user. For example, when the motion factor is processed as a vital-sign factor, the smartphone 1 performs processes such as calculation and output based on the detected motion factor. The output includes display on the display 2A and transmission to a server or the like. In this embodiment, different control is performed between the first mode and the second mode, but this disclosure is not limited to this example. For example, when the control mode of the controller 10 is changed to the second mode, a new process in addition to the process in the first mode may be performed.

Sensors in which three directions are orthogonal to each other are employed as the acceleration sensor 16 and the angular velocity sensor 18 in this embodiment, but three directions may not be orthogonal to each other. An acceleration sensor and an angular velocity sensor in which three directions are not orthogonal to each other can calculate acceleration and angular velocity in three orthogonal directions by calculation. The acceleration sensor and the angular velocity sensor may have different reference directions.

Some or all of the programs stored in the storage 9 in FIG. 5 may be downloaded from another device through wireless communication by the communication unit 6. Some or all of the programs stored in the storage 9 in FIG. 5 may be stored in a storage medium which can be read by a reader included in the storage 9. Some or all of the programs stored in the storage 9 in FIG. 5 may be stored in a storage medium such as a CD, a DVD, or a Blu-ray (registered trademark) which can be read by a reader connected to the connector 14.

The configuration of the smartphone 1 illustrated in FIG. 5 is an example and may be appropriately changed without damaging the gist of this disclosure. For example, the number or the type of buttons 3 is not limited to the example illustrated in FIG. 5. For example, the smartphone 1 may include ten-key or QWERTY buttons as buttons for operation on a screen instead of the buttons 3A to 3C. The smartphone 1 may include only a single button or may not include a button for operation on a screen. In the example illustrated in FIG. 5, the smartphone 1 includes two cameras, but the smartphone 1 may include only a single camera or may not include any camera. The illuminance sensor 4 and the proximity sensor 5 may configured by a single sensor. In the example illustrated in FIG. 5, the smartphone 1 includes three types of sensors for detecting the position and the posture, but the smartphone 1 may not include some sensors of that sensors or may include another type of sensor for detecting the position and the posture.

An example in which the smartphone 1 measures a vital sign of a user using the measuring application 9Z will be described below.

Figure 6:
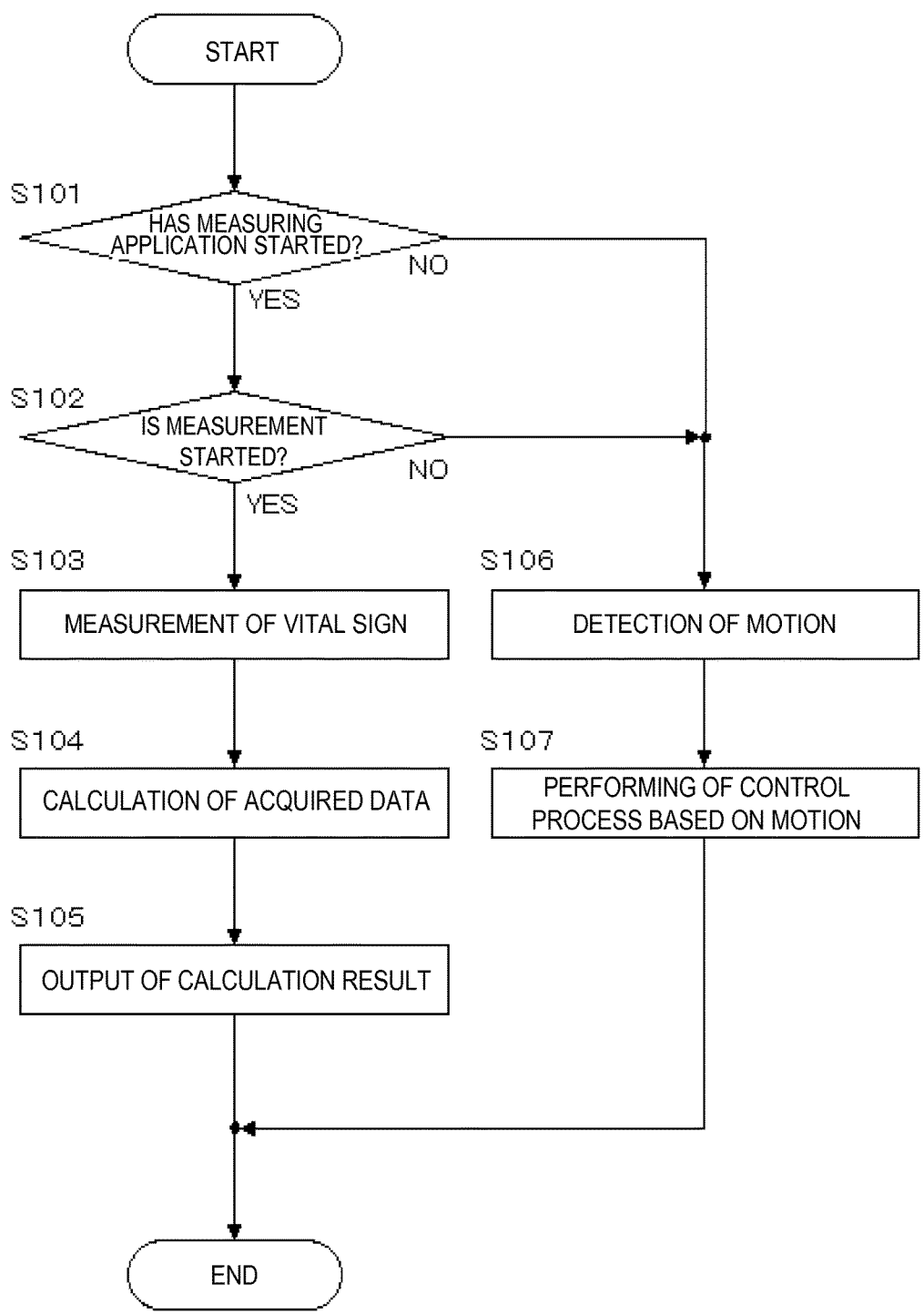
FIG. 6 is a view illustrating an example of a control flow which is performed by the smartphone according to the embodiment.

FIG. 6 is a view illustrating a first example of a flow which is performed by the smartphone according to this embodiment. The flow illustrated in FIG. 6 is performed by cooperation with the basic program 9A and the measuring application 9Z. The smartphone 1 proceeds to step S102 or step S106 depending on whether the measuring application 9Z has started as described in step S101. The processes of steps S101, S106, and S107 are performed based on the basic program 9A, and the processes of steps S102 to S105 are performed based on the measuring application 9Z. The measuring application 9Z can be started, for example, by tapping an icon 51 illustrated in FIG. 5.

Figure 7:
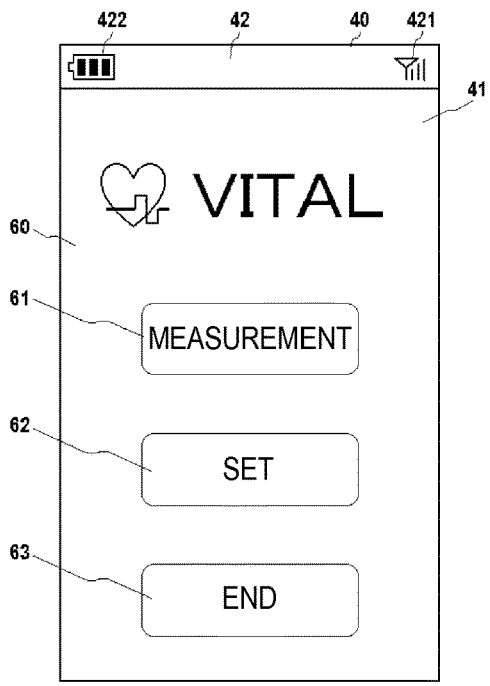
FIG. 7 is a view illustrating an example of an execution screen of an application in the smartphone according to the embodiment.
Figure 8:
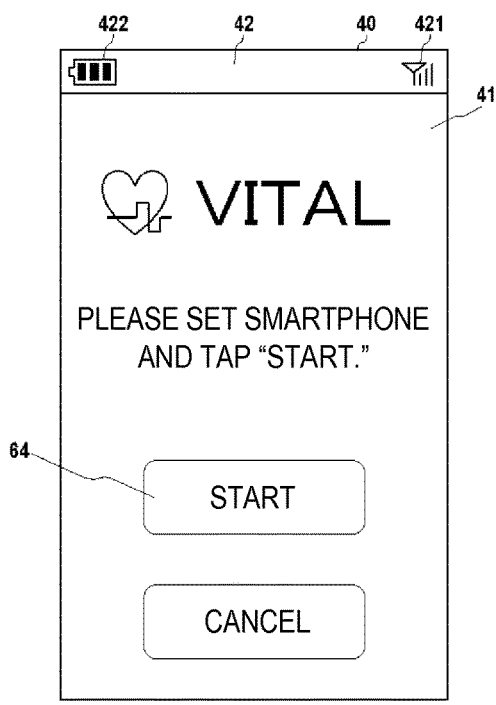
FIG. 8 is a view illustrating an example of an execution screen of an application in the smartphone according to the embodiment.

When the measuring application 9Z is started, the smartphone 1 displays, for example, an operation screen 60 of an application illustrated in FIG. 7 in the first area 41. The smartphone 1 transitions to a screen capable of starting measurement of a vital sign when an icon 61 is tapped, transitions to a screen capable of changing setting of the measuring application 9Z when an icon 62 is tapped, and ends the measuring application 9Z when an icon 63 is tapped. The smartphone 1 checks whether the measurement of a vital sign has started in step S102. An example of the screen capable of starting measurement of a vital sign is illustrated in FIG. 8. When an icon 64 in the example illustrated in FIG. 8 is tapped, the smartphone 1 starts measurement of a vital sign. The smartphone 1 proceeds to step S103 when the measurement of a vital sign is started, and proceeds to step S106 when the measurement is not started. When the flow proceeds from step S102 to step S103, the mode in which the controller 10 performs control based on the motion factor is changed from the first mode to the second mode.

In step S103, the smartphone 1 measures a vital sign of a user. In step S103, the motion factor acquired from at least one of the acceleration sensor 16 and the angular velocity sensor 18 is processed as a vital-sign factor of the user. That is, in step S103, the motion factor acquired from at least one of the acceleration sensor 16 and the angular velocity sensor 18 is processed as a vital-sign factor of the user. In this embodiment, a pulsating force based on a force extending a blood vessel due to pulsation is measured as the vital-sign factor. The pulsating force is acquired by processing the motion factor, which is acquired from at least one of the acceleration sensor 16 and the angular velocity sensor 18 when the smartphone 1 comes in contact with a measurement part, as a motion of the smartphone 1 due to the pulsating force. In step S103 in this embodiment, the control mode of the controller 10 is set to the second mode. The smartphone 1 proceeds to step S104 when the vital-sign factor is measured in step S103.

The smartphone 1 calculates acquired data, which indicates the vital sign of the user in step S103, in step S104. By the calculation of data indicating the vital sign, it is possible to calculate, for example, a pulse pressure, a continuous pulse pressure, a blood pressure, a continuous blood pressure, a pulse, and a displacement accompanied with pulsation. In the following description, the blood pressure means a systolic blood pressure (maximum blood pressure) and a diastolic blood pressure (minimum blood pressure), and the pulse pressure means a difference between the maximum blood pressure and the minimum blood pressure. The continuous pulse pressure and the continuous blood pressure mean the pulse pressure and the blood pressure in one cycle of pulsation in which contraction and extension are continuously repeated, respectively, and mean the pulse pressure and the blood pressure including continuous temporal variations, respectively. That is, in step S104, the motion factor acquired from at least one of the acceleration sensor 16 and the angular velocity sensor 18 is calculated as the vital-sign factor of the user. In step S104 in this embodiment, the control mode of the controller 10 is set to the second mode. When data indicating the vital sign is calculated, the smartphone 1 proceeds to step S105. Details of the calculation of the vital sign in step S104 will be described later.

In step S105, the smartphone 1 outputs the calculation result of step S104. Here, examples of the output of the calculation result of the vital sign include various methods such as display on the display 2B and transmission to a server collecting vital signs. That is, in step S105, the motion factor acquired from at least one of the acceleration sensor 16 and the angular velocity sensor 18 is output as the vital-sign factor of the user. In step S105 in this embodiment, the control mode of the controller 10 is set to the second mode. Here, an example in which the calculation result of the vital sign is transmitted to the server is described, but a configuration in which the measurement data indicating the vital sign is transmitted to the server may be employed. When the output of the calculation result of the vital sign ends, the smartphone 1 ends the flow.

The smartphone 1 moves the flow from step S101 or S102 to steps S106 and S107. The smartphone 1 measures a motion of the smartphone 1 in step S106. The motion of the smartphone 1 is measured using one of the acceleration sensor 16 and the angular velocity sensor 18. The smartphone 1 proceeds to step S107 when the motion is detected. In step S107, the smartphone 1 processes the motion factor corresponding to the detected motion as a control factor. In step S107, a control process based on the motion is performed.

In step S107 in this embodiment, the control mode of the controller 10 is set to the first mode. An example of this control is control of changing the display direction of the screen when the x axis direction of the smartphone 1 is parallel to the gravitational direction.

An example in which acceleration accompanied with pulsation of the user as the vital sign is measured using the acceleration sensor 16 will be described below.

Figure 9:
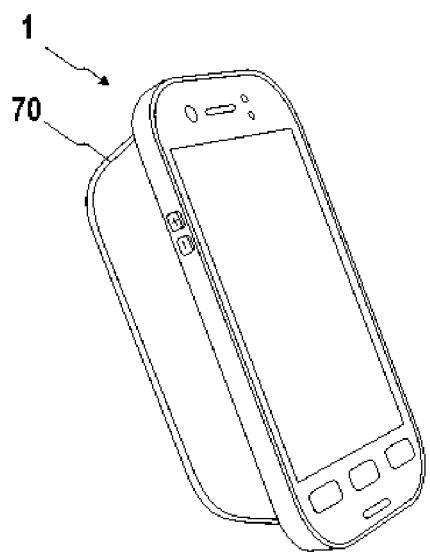
FIG. 9 is a schematic view illustrating an example in which a belt is attached to the smartphone according to the embodiment.
Figure 10:
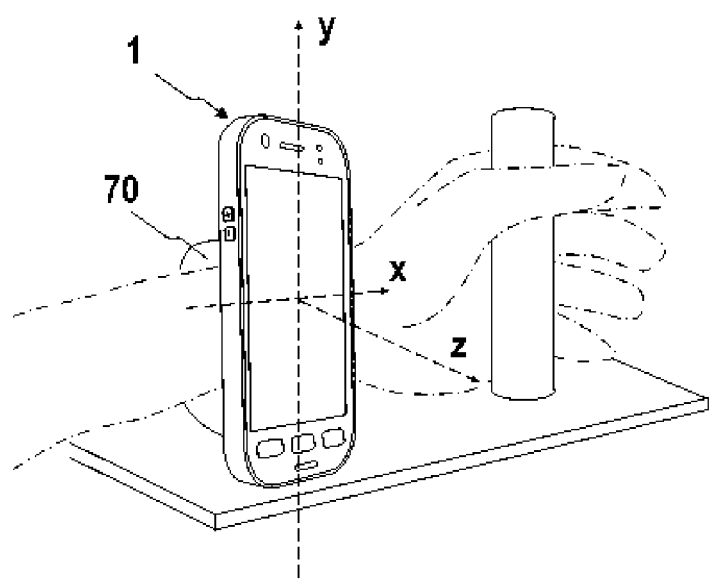
FIG. 10 is a schematic view illustrating a first example when a vital sign is measured by the smartphone according to the embodiment.
Figure 11:
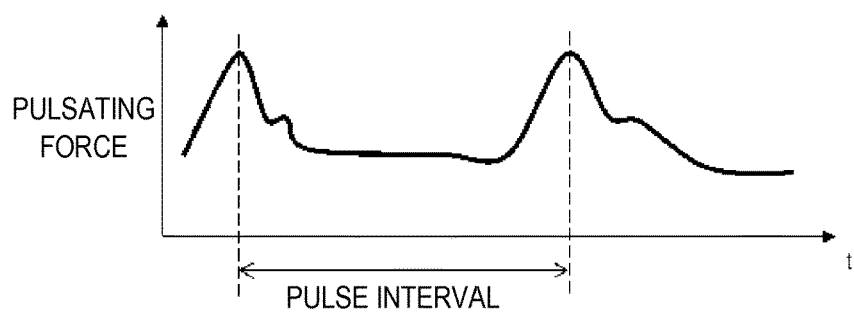
FIG. 11 is a view illustrating schematic waveforms when a vital sign is measured by the smartphone according to the embodiment.

First, a belt 70 illustrated as an example in FIG. 9 is attached to the smartphone 1. The spring constant of the belt 70 is set to a value suitable for following vibration of a pulse wave, that is, pulsation. Then, as illustrated as an example in FIG. 10, the smartphone 1 having the belt 70 attached thereto is mounted on a user's wrist and is brought into contact with a measurement part. At this time, in order to reduce complication of the control due to the gravitational force, it is preferable that the x-y plane of the smartphone 1 be substantially parallel to the gravitational direction. In this state, the acceleration sensor 16 continuously measures acceleration accompanied with pulsation of the user as the motion factor. In measuring the acceleration, it is possible to enhance measurement accuracy by grasping a fixed object or the like to stabilize the wrist as illustrated in the example of FIG. 10. Then, the controller 10 calculates a pulsating force from the acceleration having been continuously measured. An example of the continuous waveforms of the pulsating force acquired by the measurement is illustrated in FIG. 11. The method of calculating a pulsating force will be described in detail later.

The smartphone 1 calculates a continuous blood pressure P(t) from the measured acceleration based on the relationships of Expressions 1 and 2. More specifically, a pulsating force f(t) is calculated from the measured acceleration based on Expression 2. Then, the continuous blood pressure P(t) is calculated from the calculated pulsating force f(t) based on Expression 1. Expression 2 uses the following parameters and constants. f(t) denotes a pulsating force; p(t) denotes a force acting on the smartphone 1 based on a force extending a blood vessel; a(t) denotes acceleration measured by the acceleration sensor; S denotes a contact area with a radial artery; M denotes the mass of the smartphone 1; K denotes the spring constant of the belt 70; and D denotes the velocity attenuation constant of a belt 70-smartphone 1 system.

$$P(t)=A_1 \times f(t)+B_1 \qquad \text{Expression 1}$$

$$f(t)=p(t)S=Ma(t)+D\int a(t)dt+K\iint a(t)dtdt \qquad \text{Expression 2}$$

In Expression 2, the mass of a blood vessel and dermal system is considered to be much smaller than the mass M of the smartphone 1 and thus the constant M is employed as an approximate value. In the spring system of Expression 2, the spring constant of the blood vessel and dermal system is considered to be much smaller than the spring constant K of the belt 70 and thus the constant K is employed as an approximate value. In a velocity attenuation system of Expression 2, the viscous friction coefficient of the blood vessel and dermal system is considered to be much smaller than the velocity attenuation constant D of the belt 70-smartphone 1 system and thus the constant D is employed as an approximate value. The constants M, K, and D in Expression 2 employ values which have been measured in advance. The constants M, K, and D are set in advance in consideration of manufacturing errors. The smartphone 1 and the radial artery do not come in actual contact with each other, but the contact area S thereof is a parameter in calculation on the assumption that both come in contact with each other. The approximate values of the constants $A_1$ and $B_1$ in Expression 1 are calculated using the following measurement method. First, the pulsating force f(t) as a vital sign is calculated using the acceleration a(t) measured by the acceleration sensor and Expression 2. The maximum pulsating force $f_{MAX}$ and the minimum pulsating force $f_{MIN}$ are specified from the calculated pulsating force f(t). Then, the maximum blood pressure $P_{MAX}$ and the minimum blood pressure $P_{MIN}$ are measured using a general household sphygmomanometer. At this time, a sphygmomanometer which is wound on a wrist can be preferably used as the general sphygmomanometer in order to reduce a difference depending on measurement parts. Finally, the constants $A_1$ and $B_1$ are calculated from the maximum pulsating force $f_{MAX}$, the minimum pulsating force $f_{MIN}$, the maximum blood pressure $P_{MAX}$, and the minimum blood pressure $P_{MIN}$.

The blood pressure can be calculated from the pulsating force as a vital sign using the constants calculated as described above. At this time, the calculated vital sign has a continuous value having the time counted by a timer built in the controller or the like as a variable. That is, the smartphone 1 can calculate a continuous blood pressure.

An example in which acceleration accompanied with a user's pulsation as a vital sign is measured using the acceleration sensor 18 will be described below.

Figure 12:
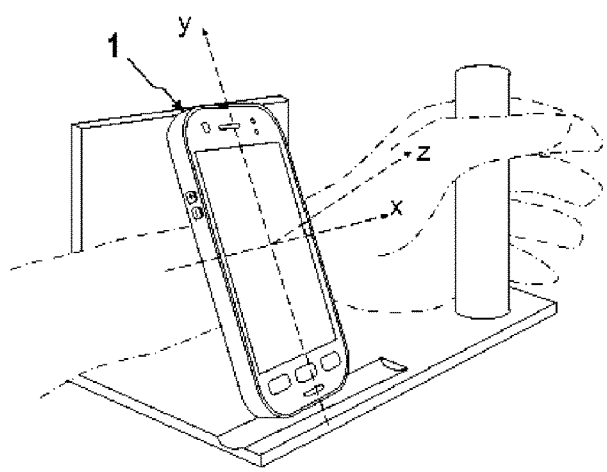
FIG. 12 is a schematic view illustrating a second example when a vital sign is measured by the smartphone according to the embodiment.
Figure 13:
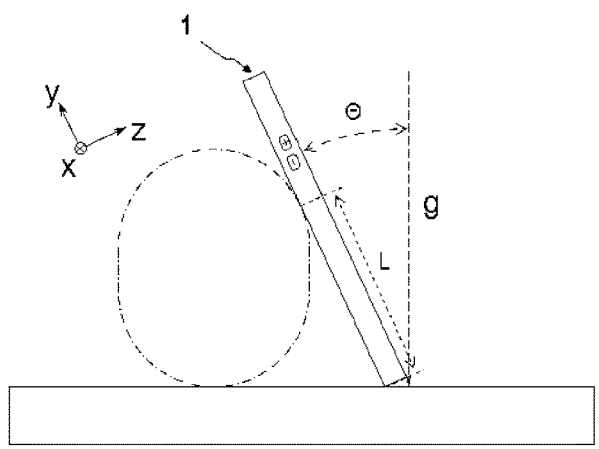
FIG. 13 is a schematic view illustrating the second example illustrated in FIG. 12 when viewed from the x axis direction.

First, as illustrated in FIGS. 12 and 13, the smartphone 1 is brought into contact with the user's wrist as a measurement part. At this time, the smartphone 1 is preferably mounted on a stage with a large friction coefficient and small rolling resistance. As an example of the stage having such characteristics is a rug formed of rubber. Then, the angular velocity sensor 18 continuously measures the acceleration accompanied with pulsation as a motion factor in this state. In measuring the angular velocity, it is possible to enhance measurement accuracy by grasping a fixed object to stabilize the wrist as illustrated in FIG. 12. Then, the controller 10 calculates a pulsating torque from the angular velocity which has been continuously measured. The method of calculating the pulsating torque will be described later in detail.

The smartphone 1 calculates a continuous blood pressure P(t) from the measured angular velocity based on the relationships of Expressions 3 and 4. More specifically, a pulsating torque f(t)L is calculated from the measured angular velocity based on Expression 4. Then, the continuous blood pressure P(t) is calculated from the calculated pulsating torque f(t)L based on Expression 3. Expression 4 uses the following parameters and constants: f(t) denotes a pulsating force; p(t) denotes a force acting on the smartphone 1 based on a force extending a blood vessel; ω(t) denotes angular velocity measured by the angular velocity sensor 18; θ denotes an initial angle with respect to the gravitational direction; S denotes a contact area with a radial artery; I denotes the moment of inertia of the smartphone 1; M denotes the mass of the smartphone 1; K denotes the spring constant of the belt 70; D denotes the velocity attenuation constant of a belt 70-smartphone 1 system; g denotes the gravitational acceleration; and L denotes a distance from a rotation center of the smartphone 1 to a contact position.

$$P(t) = A_2 \times f(t)L + B_2 \quad \text{Expression 3}$$

$$f(t)L = p(t)SL = I\frac{d}{dt}\omega(t) + D\omega(t) + K\int\omega(t)dt + MgL\sin\left(\Theta - \int\omega(t)dt\right) \quad \text{Expression 4}$$

In Expression 4, the mass of the blood vessel and dermal system is considered to be much smaller than the mass M of the smartphone 1 and thus the constant M is employed as an approximate value. In the spring system of Expression 4, the spring constant of the blood vessel and dermal system is considered to be much smaller than the spring constant K of the belt 70 and thus the constant K is employed as an approximate value. In the viscous friction coefficient of Expression 4, the viscous friction coefficient of the blood vessel and dermal system is considered to be much smaller than the velocity attenuation constant D of the belt 70-smartphone 1 system and thus the constant D is employed as an approximate value. The constants M, K, and D in Expression 4 employ values which have been measured in advance. The constants M, K, and D are set in advance in consideration of manufacturing errors. The smartphone 1 and the radial artery do not come in actual contact with each other, but the contact area S thereof is a parameter in calculation on the assumption that both come in contact with each other.

The approximate values of the constants $A_2$ and $B_2$ in Expression 3 are calculated using the following measurement method. First, the pulsating torque f(t)L as a vital sign is calculated using the angular velocity ω(t) measured by the angular velocity sensor and Expression 4. The pulsating torque f(t)L is a rotational torque accompanied with the user's pulsation. The maximum pulsating torque $fL_{MAX}$ and the minimum pulsating torque $fL_{MIN}$ are specified from the calculated pulsating torque f(t)L. Then, the maximum blood pressure $P_{MAX}$ and the minimum blood pressure $P_{MIN}$ are measured using a general household sphygmomanometer. At this time, a sphygmomanometer which is wound on a wrist can be preferably used as the general sphygmomanometer in order to reduce a difference depending on measurement parts. Finally, the constants $A_2$ and $B_2$ are calculated from the maximum pulsating torque $fL_{MAX}$, the minimum pulsating torque $fL_{MIN}$, the maximum blood pressure $P_{MAX}$, and the minimum blood pressure $P_{MIN}$.

The blood pressure can be calculated from the pulsating torque as a vital sign using the constants calculated as described above. At this time, the calculated vital sign has a continuous value having the time counted by a timer built in the controller or the like as a variable. That is, the smartphone 1 can calculate a continuous blood pressure.

If the output of the angular velocity sensor 18 is used to calculate the pulsating torque, it is possible to calculate the pulsating torque without multiplexing a differential or integral operation of the output. The smartphone 1 can reduce an influence of a rounding error in calculation to enhance accuracy by using the angular velocity sensor 18. The example of calculating the pulsating torque f(t)L has been described above, but the pulsating force f(t) may be calculated.

Figure 14:
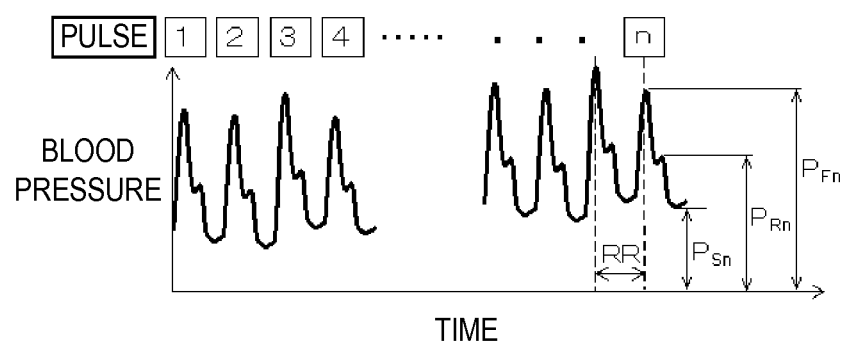
FIG. 14 is a view illustrating a calculated continuous blood pressure.

FIG. 14 is a view illustrating the continuous blood pressure P(t) which is calculated based on the detected acceleration or angular velocity, where the horizontal axis represents the time and the vertical axis represents the blood pressure. A wave obtained by a volume variation resulting from a flow of blood into a blood vessel as a waveform via a body surface is referred to as a pulse wave and the wave illustrated in FIG. 14 is called pulse wave hereinafter. The pulse wave illustrated in FIG. 14 is n pulses of the user, where n is an integer equal to or greater than 1. The controller 10 calculates the continuous blood pressure from the detected angular velocity based on Expressions 3 and 4. Alternatively, the controller 10 calculates the continuous blood pressure from the detected acceleration based on Expressions 1 and 2. Since the calculated continuous blood pressure may include noise resulting from a body motion of a user or the like, the pulsation component may be extracted by performing a correction process of removing DC components. The pulse wave is a synthesized wave in which an advancing wave generated due to ejection of blood from a heart and a reflected wave generated from a part in which a blood vessel is branched or a blood vessel diameter varies are superimposed. When the peak of the pulse wave due to the advancing wave for each pulse is defined $P_{Fn}$, the peak of the pulse wave due to the reflected wave for each pulse is defined as $P_{Rn}$, and the minimum value of the pulse wave for each pulse is defined as $P_{Sn}$, the pulse pressure is expressed by $P_{Mn}=P_{Fn}-P_{Sn}$ and $AI_n=(P_{Rn}-P_{Sn})/(P_{Fn}-P_{Sn})$. Here, AI is obtained by quantizing the magnitude of the reflected wave indicating the reflection phenomenon of a pulse wave. $AI_n$ denotes the AI for each pulse. The AI may increase for an aged person having a high pulse wave propagation speed due to advancement of arteriosclerosis. The AI can be used as an index indicating the mechanical characteristics of a blood vessel. The mechanical characteristics of a blood vessel are peripheral vascular resistance, compliance, characteristic impedance, pulse wave propagation time, and the like, and the AI can be used as an index obtained by synthesizing the characteristics.

The smartphone 1 can estimate viscoelasticity of a user's blood vessel from the vital sign calculated in this embodiment. The viscoelasticity is obtained by combining both characteristics of liquid-specific viscosity and solid-specific elasticity. The viscoelasticity represents a degree of difficulty in deformation of an object. The viscoelasticity of a blood vessel varies depending on advancement of arteriosclerosis. In order to understand a degree of advancement of arteriosclerosis, it is important to estimate the viscoelasticity of a blood vessel. However, a method of noninvasively estimating the viscoelasticity of a blood vessel is not established yet. In this embodiment, the viscoelasticity of a user's blood vessel is estimated noninvasively.

An example in which the smartphone 1 measures a motion factor of a user in accordance with a measuring application and estimates the viscoelasticity of a blood vessel of the user will be described below.

FIG. 15 is a view illustrating a flow which is performed by a smartphone 1 according to a second embodiment. The same configurations as in the first embodiment illustrated in FIG. 6 will not be described and differences therebetween will be described below. Although not illustrated in FIG. 15, the smartphone 1 may process a motion factor corresponding to a detected motion as a control factor.

The flow illustrated in FIG. 15 is performed by the basic program 9A and a measuring application 9Y in cooperation with each other. The measuring application 9Y detects a motion factor as numerical information indicating a biological sign of a user using the smartphone 1. The measuring application 9Y calculates a vital sign by processing the detected motion factor as a vital-sign factor. The measuring application 9Y provides a function of estimating the viscoelasticity of a blood vessel from the calculated vital sign. Examples of the vital sign calculated in this embodiment include a blood pressure, a pulse pressure, a pulsating force, and a displacement accompanied with pulsation.

When the measuring application 9Y has started in step S201, the smartphone 1 moves the flow to step S202. In step S202, the smartphone 1 instructs a measurer to start avascularization. The instruction to start the avascularization may be displayed on the display 2A of the smartphone 1 or may be announced by voice. The measurer performs avascularization of a user in response to the instruction to start avascularization. The avascularization is to hinder a bloodstream into a measurement part. In this embodiment, the avascularization is performed to hinder a bloodstream into the measurement part in the artery. The avascularization is performed by winding up a rubber band or the like on a position closer to the heart from the measurement part from which the motion factor is detected. For example, when the measurement part is the radial artery, the avascularization position is preferably set to an upper arm. The avascularization may use a commercial tourniquet. The winding strength of the tourniquet is preferably set such that the pulsation amplitude (corresponding to a pulse pressure) of the radial artery is less than about a half before the winding. By using a device capable of controlling the winding strength of the tourniquet so as to be constant with a pressure sensor or the like, the smartphone 1 can reduce a measurement error by measurers or users. The avascularization method is not limited to the winding of the rubber band or the like, but may employ an air pressure. The method of hindering a bloodstream into the measurement part is not limited to the avascularization, as long as the bloodstream into the measurement part can be temporarily hindered. For example, a user may hinder a bloodstream by raising the measurement part higher than the heart and may open the bloodstream by lowering the measurement part lower than the heart.

The smartphone 1 detects start of avascularization in step S203 after instructing the avascularization in step S202. The measurer can information the smartphone 1 of the start of avascularization by touching a screen of the smartphone 1 or the like. The smartphone 1 continuously instructs the avascularization until detecting the start of avascularization.

When the start of avascularization is detected in step S203, the smartphone 1 starts measurement of a vital sign (step S204). The smartphone 1 detects a motion factor from at least one of the acceleration sensor 16 and the angular velocity sensor 18 and processes the detected motion factor as a vital-sign factor of the user. In this embodiment, a pulsating force based on a force extending a blood vessel due to pulsation is measured as the vital sign. The pulsating force is obtained by processing the motion factor, which is acquired from at least one of the acceleration sensor 16 and the angular velocity sensor 18 when the smartphone 1 is brought into contact with the measurement part, as a motion of the smartphone 1 due to the pulsating force. In step S204, the smartphone 1 starts counting of the measurement time using a timer at the same time as starting the measurement of the vital sign. The timer outputs a clock signal of a predetermined frequency. The timer outputs the clock signal to the controller 10 in response to a timer operation instruction from the controller 10. At least one of the acceleration sensor 16 and the angular velocity sensor 18 detects the motion factor plural times in response to the clock signal input from the controller 10. The timer may be disposed outside the controller 10 or may be included in the controller 10. When the measurement of the vital sign has started, the smartphone 1 moves the flow to step S205.

The smartphone 1 instructs the measurer to release the avascularization in step S205. The instruction to release the avascularization may be displayed on the display 2A of the smartphone 1 or may be announced by voice. The conditions for releasing the avascularization are appropriately set. For example, the conditions for releasing the avascularization may be set to a case in which the pulsation amplitude is equal to or less than a predetermined magnitude. For example, the smartphone 1 determines that the magnitude of the pulsation amplitude is equal to or less than the predetermined magnitude when the pulsation amplitude is equal to or less than a half of the pulsation amplitude before the avascularization. Alternatively, the conditions for releasing the avascularization may be set to a predetermined elapsed time after the start of avascularization. The predetermined elapsed time is set to a time in which the pulsation amplitude after the avascularization sufficiently becomes equal to or less than the predetermined magnitude. The time from the start of avascularization to the release of avascularization is about several seconds.

The smartphone 1 detects the releasing of avascularization in step S206 after instructing to release the avascularization in step S205. The measurer can inform the smartphone 1 of the release of avascularization by touching the screen of the smartphone 1 or the like. The smartphone 1 continuously instructs to release the avascularization until detecting the release of avascularization.

When the release of avascularization is detected in step S206, the smartphone 1 ends the measurement of the vital sign after a predetermined time elapses (step S207). The predetermined time is set in consideration of at least the time until the pulsation amplitude is stabilized. The time from the release of avascularization to stabilization of the pulsation amplitude is about several seconds. The smartphone 1 may predict the time from the release of avascularization to stabilization of the pulsation amplitude and may automatically end the measurement when the predicted time elapses. In this embodiment, the start and end of measurement are performed based on the measurer's informing of the smartphone 1, but this disclosure is not limited to this configuration. For example, the smartphone 1 may start the measurement of a vital sign at the same time as starting the measuring application 9Y. For example, the smartphone 1 may automatically detect the release of the avascularization and the stabilization of the pulsation amplitude based on the measured vital-sign factor and may end the measurement.

The controller 10 calculates the vital sign of the user in step S208. By calculating the vital-sign factor, the controller 10 can calculate a vital sign such as a pulsating force, a pulse pressure, a continuous pulse pressure, a blood pressure, a continuous blood pressure, a pulse, and a displacement accompanied with pulsation. In step S208, the controller processes the motion factor acquired from at least one of the acceleration sensor 16 and the angular velocity sensor 18 as the vital-sign factor of the user and calculates the vital sign. The process of step S208 in this embodiment is an example of calculating the continuous blood pressure and the displacement accompanied with pulsation. When the vital-sign factor is calculated, the smartphone 1 moves the flow to step S209. The calculation of the vital-sign factor in step S208 is the same as in step S104 of FIG. 6 and thus will not be repeated herein.

The smartphone 1 estimates the viscoelasticity of a blood vessel of the user, from the continuous blood pressure and the displacement accompanied with pulsation, which are calculated in step S208, in step S209. The estimation of the viscoelasticity of a blood vessel in step S209 will be described later in detail.

In step S210, the smartphone 1 outputs the results of the vital sign calculated in step S208 and the viscoelasticity of a blood vessel estimated in step S209. When the output of the results is ended, the smartphone 1 ends the flow. The measurer performs the measurement in the above-mentioned flow, but the user may perform the measurement.

Figure 16A:
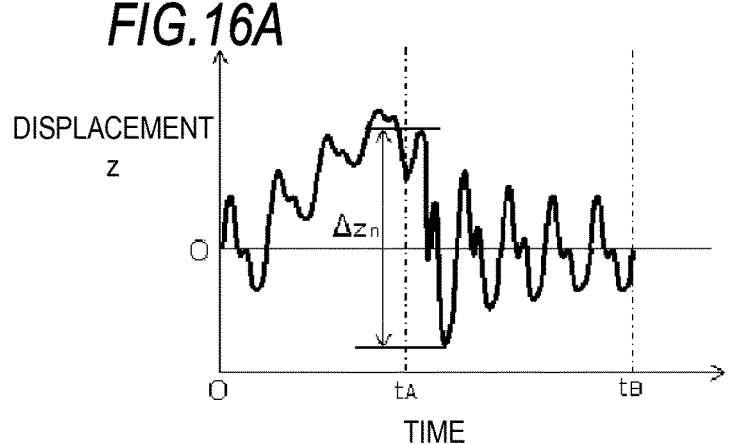
FIG. 16A and FIG. 16B are diagrams illustrating a calculated variation accompanied with pulsation and a calculated continuous blood pressure.
Figure 16B:
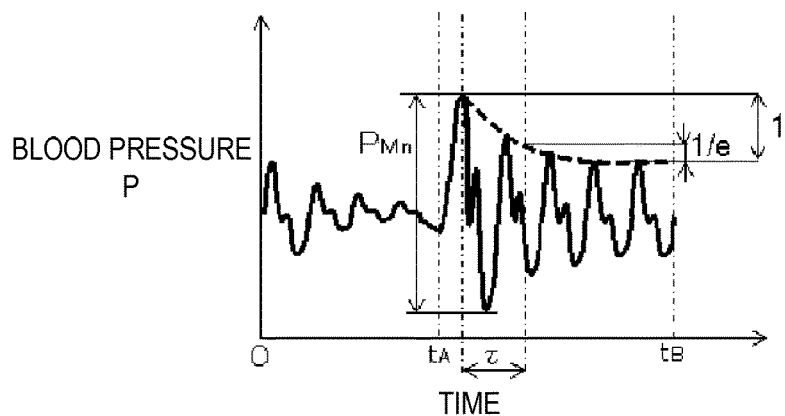

FIG. 16A and FIG. 16B are views illustrating the displacement accompanied with pulsation and the continuous blood pressure, which are calculated based on the angular velocity measured in the above-mentioned flow. The horizontal axis represents the time and the vertical axis represents the continuous blood pressure just after the avascularization has started.

FIG. 16A is a view illustrating a relationship between the displacement accompanied with pulsation and the time. The displacement accompanied with pulsation z is calculated by integrating the angular velocity $\omega(t)$ measured by the angular velocity sensor 18 of the smartphone 1 with respect to the time with an initial value set to 0. Since a bloodstream is hindered at the same time as starting the avascularization, the blood vessel expands and the pulse pressure decreases. Accordingly, the displacement accompanied with pulsation z slowly increases and the displacement $\Delta z$ corresponding to the pulse pressure slowly decreases (between 0 second and $t_A$ seconds in FIG. 16A). Here, n denotes the pulse and is an integer equal to or greater than 1. When the avascularization is released at $t_A$ seconds, the hindered bloodstream flows in the blood vessel at a time and thus the pulse pressure increases and is slowly restored to a normal state. Therefore, the displacement $\Delta z_n$ corresponding to the pulse pressure after the avascularization is released becomes the maximum and then slowly decreases to a normal state (between $t_A$ seconds and $t_B$ seconds in FIG. 16A).

The solid line illustrated in FIG. 16B denotes the calculated continuous blood pressure P(t). The continuous blood pressure P(t) is calculated using Expressions 3 and 4. The calculated continuous blood pressure P(t) is subjected to a correction process of removing a DC component so as to remove noise resulting from a body motion of the user or the like therefrom. As a result, the continuous blood pressure P(t) illustrated in FIG. 16B is acquired by extracting a pulse pressure component. Since the start of avascularization may hinder a bloodstream, the pulse pressure $P_M$ slowly decreases (between 0 second and $t_A$ seconds in FIG. 16B). When the avascularization is released at $t_A$ seconds, the hindered bloodstream flows in the blood vessel at a time and thus the pulse pressure $P_{Mn}$ is the maximum after the avascularization is released and slowly decreases to the normal state (between $t_A$ seconds and $t_B$ seconds in FIG. 16B).

Then, the smartphone 1 estimates the viscoelasticity of a blood vessel of the user. Since a blood vessel exhibits behavior of both elasticity and viscosity, the smartphone 1 can estimate the viscoelasticity of a blood vessel by calculating a coefficient of elasticity and a coefficient of viscosity.

The elasticity of a blood vessel can be estimated from stress to the blood vessel and deformation thereof. In this embodiment, the smartphone 1 calculates the coefficient of elasticity E to estimate the elasticity of the blood elasticity. The coefficient of elasticity E is estimated based on the calculated pulse pressure $P_{Mn}$ (stress to a blood vessel wall) and the calculated displacement accompanied with pulsation $\Delta z_n$ (deformation). The coefficient of elasticity E is estimated from the relationship of the coefficient of elasticity $E = P_{Mn}/\Delta z_n$. The pulse pressure $P_{Mn}$ and the displacement accompanied with pulsation $\Delta z_n$ are the pulse pressure and the displacement accompanied with pulsation in the same pulse. Here, n denotes the pulse and is an integer equal to or greater than 1. When the pulse pressure and the displacement accompanied with pulsation are large, the measurement error further decreases and it is thus preferable that the pulse pressure $P_{Mn}$ and the displacement accompanied with pulsation $\Delta z_n$ be extracted from the first pulse after the avascularization is released.

The viscosity of a blood vessel can be estimated from the behavior of the blood vessel after the avascularization is released. In this embodiment, the smartphone 1 estimates the viscosity of a blood vessel by calculating the coefficient of viscosity $\gamma$. The coefficient of viscosity $\gamma$ is estimated based on a relationship between the time after the avascularization is released and the vital sign corresponding to the time after the avascularization is released. In FIG. 16B, the vital sign corresponding to the time after the avascularization is released is the maximum blood pressure, for each pulse. The dotted line illustrated in FIG. 16B is an attenuation curve which is obtained by approximating the relationship between the maximum blood pressure and the time, for each pulse after the avascularization is released using a least square method. The coefficient of viscosity $\gamma$ of a blood vessel is estimated from the time constant $\tau$ induced from the attenuation curve and the coefficient of elasticity E. The coefficient of viscosity $\gamma$ of a blood vessel is estimated by $\gamma = E \times \tau$. The time constant $\tau$ is set to a time at which the value indicated by the attenuation curve is 1/e (where e denotes the base of the natural logarithm) with respect to the time at which the blood pressure after the avascularization is the maximum.

In the above-mentioned embodiment, the coefficient of elasticity and the coefficient of viscosity of a blood vessel are calculated to estimate the viscoelasticity of the blood vessel, but this disclosure is not limited to this configuration. At least one of the coefficient of elasticity and the coefficient of viscosity of a blood vessel may be calculated to estimate the viscoelasticity of the blood vessel. In the above-mentioned embodiment, the maximum blood pressure, for each pulse is used as the vital sign corresponding to the time after the avascularization is released, but this disclosure is not limited to this configuration. The maximum pulse pressure, the maximum pulsating force, or the maximum variation accompanied with pulsation, for each pulse may be used as the vital sign corresponding to the time after the avascularization is released.

In this embodiment, since the sensor of the smartphone 1 is used, the device is small, the viscoelasticity of a blood vessel can be estimated noninvasively, and it is possible to understand a degree of advancement of arteriosclerosis of a user. Since the measurement time is several minutes and the measurement can be performed for a short time, it is possible to reduce a physical burden of the user.

Figure 17:
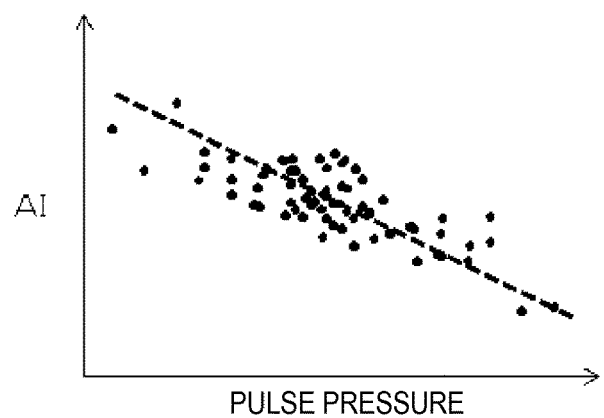
FIG. 17 is a view illustrating a relationship between a pulse pressure and an AI.

A method of estimating a blood pressure reflecting function of a user from the calculated continuous blood pressure will be described below with reference to FIG. 17. FIG. 17 illustrates a plot of the relationship between the pulse pressure as a first index and the AI as a second index, where the dotted line indicates a regression line.

The blood pressure reflecting function of a user can be estimated from the vital sign calculated in this embodiment. The blood pressure reflecting function is a reflection system for maintaining a value of a blood pressure within a predetermined range through the use of an autonomic function. In general, when a blood pressure increases, the pulse reflectively decreases, a contractile force of a myocardium decreases, the blood vessel is extended, and the blood pressure decreases and is returned to a normal value. This function is called blood pressure reflecting function. The decrease in the blood pressure reflecting function is one reason of hypertension. Accordingly, in order to understand the reason of hypertension, it is important to estimate the blood pressure reflecting function. In this embodiment, it is possible to noninvasively estimate the blood pressure reflecting function without using large-sized equipment.

The controller 10 calculates pulse pressures $P_{M1}$ to $P_{Mn}$, for each pulse as the first index and $AI_1$ to $AI_n$, for each pulse as the second index corresponding to the pulse wave reflection phenomenon from the continuous blood pressure P(t) calculated based on the detected motion factor (angular velocity in this embodiment). As described above, n denotes the measured pulse and the pulse pressure and the AI are associated with each other, for each pulse. The pulse pressure is a difference between the peak $P_F$ of the pulse wave due to the advancing wave and the minimum value $P_S$ of the pulse wave, and can be preferably used as the first index because the influence of noise due to the body motion or the device can be reduced. The AI is a ratio of the peak $P_F$ of the pulse wave due to the advancing wave and the peak $P_R$ of the pulse wave due to the reflected wave, and can be preferably used as the second index because the influence of noise due to the body motion or the characteristics of the sensor itself can be reduced.

The controller 10 estimates the regression line from n sets of the pulse pressure $P_M$ and the AI associated with each other. When the pulse pressure increases, the blood vessel expands due to the blood pressure reflecting function of the blood vessel and the AI which is obtained by quantizing the magnitude of the reflected wave decreases. Accordingly, it is possible to estimate the blood pressure reflecting function of the blood vessel based on the slope of the regression line. That is, it is estimated that the closer the slope of the regression line becomes to zero, the lower the sensitivity of the blood pressure reflecting function of the blood vessel becomes.

In this embodiment, since the sensor of the smartphone 1 is used, the device has a small size and the blood pressure reflecting function of the blood vessel can be estimated noninvasively. The blood pressure reflecting function can be estimated from several tens of sets of data and the measurement time is several minutes. Accordingly, the blood pressure reflecting function can be measured for a short time. Data of the blood pressure having a magnitude gap can be preferably used in view of accuracy of the regression line. Therefore, the blood pressure may be intentionally changed by giving stimulation to the user in measurement using a video or the like. By using the pulse pressure as the first index and using the AI as the second index, it is possible to reduce an influence of noise due to the body motion or the device and thus to perform estimation with high accuracy. By using the AI as the second index, it is possible to collectively estimate the mechanical characteristics of a blood vessel.

In the above-mentioned embodiment, the angular velocity is detected as the motion factor, but the acceleration may be detected or any continuous motion accompanied with pulsation can be detected. The pulse pressure is used as the first index, but this disclosure is not limited to this configuration. The first index only has to be an index calculated from the motion factor and may be a blood pressure, a pulsating force, a pulsating torque, a displacement angle calculated from the angular velocity, or a displacement calculated from the acceleration. The second index only has to be an index based on the reflection phenomenon of a pulse wave, and the peak $P_R$ of the pulse wave due to a reflected wave may be used. Depending on the first index and the second index, the blood pressure reflecting function may be estimated using a regression coefficient by performing regression analysis.

In the above-mentioned embodiment, the blood pressure reflecting function of a blood vessel is estimated, but this disclosure is not limited to this configuration. For example, it is possible to estimate the blood pressure reflecting function of a heart by performing regression analysis using a pulse interval RR as the second index. This is to estimate a reflection function in which a pulse decreases reflectively when the pulse pressure increases. For example, it is possible to estimate stress and pain of a user by performing frequency analysis based on the pulse wave calculated as the first index. As described above, in this embodiment, it is possible to estimate the autonomic function of a user based on the first index calculated from the motion factor or based on the correlation between the first index and the second index.

Specific embodiments have been described above to completely and clearly disclose this disclosure. However, the appended claims are not limited to the above-mentioned embodiments, but can implement all modifications and replaceable configurations which can be made by those skilled in the art within the basic scope of the specification.

In the above-mentioned embodiments, the smartphone 1 may determine whether the measured vital-sign factor is normal between step S103 and step S104. Whether the measured vital-sign factor is normal is determined depending on whether a deviation of data indicating the vital sign is greater than a predetermined value. For example, when a side along the x direction is placed on a plane and the vital-sign factor is measured using the angular velocity having the x direction as an axis, the values of the angular velocity having the x direction and the y direction as axes do not vary in ideal measurement. When the values of the angular velocity having the x direction and the y direction as axes vary greatly, there is a high possibility that normal data are not measured and abnormal data are measured. In this case, a display may be carried out to discard the measured data and to promote re-measurement or measurement of new data may be started.

In the above-mentioned embodiment, steps S103 and S104 are described to be independent steps, but these steps may be performed in parallel. An example in which the steps are performed in parallel is a case in which calculation is sequentially performed based on the measured data.

In the above-mentioned embodiment, in step S103, the vital-sign factor of a user is measured using at least one of the acceleration sensor 16 and the angular velocity sensor 18, but means for measuring the vital sign is not limited to these sensor. For example, by bringing a user's arm into contact with the front face 1A of the smartphone 1, the touch screen 2B can be used to measure the vital sign. Examples of information detected by the touch screen 2B which can be used to measure the vital sign include the vital sign of the user, position information of the touch screen 2B, a variation in capacitance of the touch screen 2B, and a load on the touch screen 2B. For example, the position information of the touch screen 2B can be used to grasp the contact position of the smartphone 1 with the wrist of the user. By grasping the contact position with the wrist of the user, it is possible to reduce an error of a calculation parameter resulting from the mass eccentricity of the smartphone 1. By detecting the variation in capacitance in the touch screen 2B or detecting the load on the touch screen 2B, it is possible to determine whether the contact of the smartphone 1 with the wrist of the user is stable.

In the above-mentioned embodiments, the smartphone is described as an example of a portable device that measures a vital sign, but the device described in the appended claims is not limited to the smartphone. For example, the device described in the appended claims may be portable electronic devices such as a mobile phone, a portable personal computer, a digital camera, a media player, an electronic book reader, a navigator, and a game machine.

In Expression 2, the approximate values are employed as the coefficient of elasticity and the attenuation coefficient. The coefficient of elasticity $K_0$ and the coefficient of attenuation $D_0$ in Expression 2 can be more accurately calculated using a step response method. In the step response method, forcible vibration is generated in a state where the smartphone 1 is attached to the user's wrist using the belt 70, and the coefficient of elasticity $K_0$ and the coefficient of attenuation $D_0$ can be calculated from the variation in amplitude when the vibration is attenuated. The coefficients measured using the step response method may be employed by Expression 2.

When the value of the contact area S between the smartphone 1 and the radial artery can be measured, the continuous blood pressure P(t) can be directly calculated from Expression 2 or 4.

The smartphone 1 according to this embodiment may store the angle θ with respect to the gravitational direction when the constants $A_1$ and $B_1$ or the constants $A_2$ and $B_2$ are calculated as a reference angle $θ_0$. The smartphone 1 compares the measured angle $θ_x$ when the vital sign is measured and the reference angle $θ_0$, before the vital sign is measured in step S103. Since the difference between the measured angle $θx$ and the reference angle $θ_0$ is greater than a predetermined range, there is a high possibility that the contact state of the smartphone 1 with the user greatly differs and the calculated constants A and B are greatly offset. In this case, the smartphone 1 may stop measurement of the vital sign or may promote re-adjustment of the set state of the smartphone 1.

In the above-mentioned embodiment, the smartphone 1 is brought into direct contact with the measurement part, but a member may be interposed between the measurement part and the smartphone 1. For example, a member capable of delivering a motion of a user may be interposed therebetween and a motion of the member may be measured as a vital sign of the user.

In the above-mentioned embodiments, the smartphone 1 includes the motion sensor and the controller, but the motion sensor and the controller may be included in another device. In this case, a system is configured by a device including the motion sensor and a device including the controller.

This disclosure may have the following configurations.

A device according to this disclosure includes a motion sensor, which detects a motion factor and a controller, which processes the motion factor detected by the motion sensor, and the controller calculates a vital-sign factor of a user based on the motion factor.

In the device according to this disclosure, the motion sensor detects at least one of acceleration and angular velocity as the motion factor and the controller calculates at least one of a pulsating force and a pulsating torque based on at least one of the acceleration and the angular velocity.

In the device according to this disclosure, the motion sensor detects at least one of continuous acceleration and continuous angular velocity as the motion factor and the controller calculates at least one of a continuous pulsating force and a continuous pulsating torque based on at least one of the continuous acceleration and the continuous angular velocity.

In the device according to this disclosure, the controller calculates at least one of a blood pressure, a pulse pressure, a pulse, and a displacement accompanied with pulsation of the user, based on the motion factor.

In the device according to this disclosure, the motion sensor detects at least one of continuous acceleration and continuous angular velocity as the motion factor and the controller calculates a continuous blood pressure based on at least one of the continuous acceleration and the continuous angular velocity.

In the device according to this disclosure, the motion sensor detects continuous pulsation as the motion factor and the controller calculates a continuous blood pressure based on the continuous pulsation.

In the device according to this disclosure, the motion sensor detect continuous pulsation as the motion factor and the controller calculates a continuous pulse pressure based on the continuous pulsation.

In the device according to this disclosure, the motion sensor detects continuous pulsation as the motion factor and the controller calculates continuous acceleration based on the continuous pulsation.

In the device according to this disclosure, the motion sensor detects a pulse pressure and a displacement accompanied with pulsation as the motion factor and the controller estimates viscoelasticity of a blood pressure of the user, based on the pulse pressure and the displacement accompanied with pulsation.

In the device according to this disclosure, the controller estimates viscoelasticity of a blood vessel of the user, based on a relationship between a time after a bloodstream is opened and a vital sign corresponding to the time after the bloodstream is opened.

In the device according to this disclosure, the vital sign corresponding to the time after the bloodstream is opened is a maximum blood pressure, a maximum pulsating force, a maximum pulse pressure, or a maximum displacement accompanied with pulsation, for each pulse of the user.

In the device according to this disclosure, the controller estimates a regression line from plural sets including a first index calculated from the motion factor and a second index that is corresponding to the first index and based on a reflection phenomenon of a pulse wave, and estimates a blood pressure reflecting function of the user, from a slope of the estimated regression line.

In the device according to this disclosure, the controller calculates a vital sign of the user, based on the motion factor which is detected by the motion sensor when the device is brought into contact with a part of the user.

In the device according to this disclosure, the controller calculates a vital sign of the user, based on the motion factor which is detected by the motion sensor when the device is brought into contact with a radial artery of the user.

In the device according to this disclosure, the controller calculates a continuous vital sign based on a continuous motion factor detected by the motion sensor.

In the device according to this disclosure, the controller calculates at least one of a blood pressure and a pulse of the user, from the motion factor detected by the motion sensor.

A control method of a device according to this disclosure is a control method of a device including a motion sensor, which detects a motion factor and a controller, which processes the motion factor detected by the motion sensor, the control method includes a step of calculating a vital sign of a user based on the motion factor.

The control method of the device according to this disclosure includes a step in which the motion sensor detects at least one of acceleration and angular velocity as the motion factor and the controller calculates at least one of a pulsating force and a pulsating torque based on at least one of the acceleration and the angular velocity.

The control method of the device according to this disclosure includes a step in which the motion sensor detects a continuous acceleration and continuous angular velocity as the motion factor and the controller calculates at least one of a continuous pulsating force and a continuous pulsating torque based on at least one of the continuous acceleration and the continuous angular velocity.

A control program of a device according to this disclosure is a control program of a device including a motion sensor, which detects a motion factor and a controller, which processes the motion factor detected by the motion sensor, the control program causes the controller to calculate a vital sign of a user based on the motion factor.

While this disclosure have been described in details with reference to specific embodiments, it is obvious to those skilled in the art that this disclosure can be modified or corrected in various forms.

Priority is claimed on Japanese Patent Application No. 2013-085964, filed Apr. 16, 2013, Japanese Patent Application No. 2013-177107, filed Aug. 28, 2013, Japanese Patent Application No. 2014-016044, filed Jan. 30, 2014, and Japanese Patent Application No. 2014-036931, filed Feb. 27, 2014, the contents of which are incorporated herein by reference.

REFERENCE SIGNS LIST 1 smartphone
2 touch screen display
2A display
2B touch screen
3 button
4 illuminance sensor
5 proximity sensor
6 communication unit
7 receiver
8 microphone
9 storage
9A basic program
9B mail application
9C browser application
9Z measuring application
10 controller
12, 13 camera
14 connector
15 motion sensor
16 acceleration sensor
17 bearing sensor
18 angular velocity sensor
19 angle sensor
20 housing
40 display area
41 first area
42 second area
50 home screen
51 icon
60 operation screen
61, 62, 63, 64 icon
70 belt

The invention claimed is:

1. A method of controlling a device having a sensor and a housing on which the sensor is mounted, the method comprising:
   detecting an angular movement of the housing as a detection value or a continuous detection value while the housing is in a leaning state; and
   calculating a vital sign of the user based on the detection value or the continuous detection value, wherein
   the detection value is at least one of acceleration and angular velocity of the device,
   the continuous detection value is at least one of continuous acceleration and continuous angular velocity,
   the leaning state is a state where a contact portion of the housing is in contact with a detected part of a user and a predetermined portion of the device is in contact with a stage, which is independent from the movement of the housing, and
   the vital sign is at least one of a blood pressure, a pulse pressure, a pulse, and a pulsating force.

2. A non-transitory computer-readable medium having instructions to control a device having a sensor and a housing on which the sensor is mounted, the instructions causing the device to perform:
   detecting an angular movement of the housing as a detection value or a continuous detection value while the housing is in a leaning state; and
   calculating a vital sign of the user based on the detection value or the continuous detection value, wherein
   the detection value is at least one of acceleration and angular velocity of the device,
   the continuous detection value is at least one of continuous acceleration and continuous angular velocity, the leaning state is a state where a contact portion of the housing is in contact with a detected part of a user and a predetermined portion of the device is in contact with a stage, which is independent from the movement of the housing, and the vital sign is at least one of a blood pressure, a pulse pressure, a pulse, and a pulsating force.

\* \* \* \* \*